(12) United States Patent
Tashiro

(10) Patent No.: US 10,275,897 B2
(45) Date of Patent: Apr. 30, 2019

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventor: Hideyasu Tashiro, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 17 days.

(21) Appl. No.: 15/602,721

(22) Filed: May 23, 2017

(65) Prior Publication Data

US 2017/0345168 A1 Nov. 30, 2017

(30) Foreign Application Priority Data

May 26, 2016 (JP) ................................ 2016-105514

(51) Int. Cl.
| | |
|---|---|
| G06T 7/00 | (2017.01) |
| G06T 7/40 | (2017.01) |
| G01N 21/57 | (2006.01) |
| G06T 11/60 | (2006.01) |
| H04N 5/225 | (2006.01) |

(52) U.S. Cl.
CPC ............... *G06T 7/40* (2013.01); *G01N 21/57* (2013.01); *G06T 11/60* (2013.01); *H04N 5/2256* (2013.01)

(58) Field of Classification Search
None
See application file for complete search history.

(56) References Cited

U.S. PATENT DOCUMENTS

| | | | |
|---|---|---|---|
| 2005/0179902 A1* | 8/2005 | Kadowaki | G01N 21/55 356/445 |
| 2012/0032973 A1* | 2/2012 | Sano | G01J 3/504 345/593 |

(Continued)

FOREIGN PATENT DOCUMENTS

JP 2005-227197 A 8/2005

*Primary Examiner* — Delomia L Gilliard
(74) *Attorney, Agent, or Firm* — Carter, DeLuca & Farrell LLP

(57) ABSTRACT

The image processing apparatus of the present invention is an image processing apparatus that generates gloss intensity distribution image data indicating a gloss intensity distribution based on captured image data obtained by capturing an image of a subject having concavity/convexity irradiated by a surface light source. The image processing apparatus sets an area, in which specularly reflected light from the surface light source enters a planar mirror and which is the same size as or smaller than that of an area captured by an image capturing apparatus in a case where the planar mirror is arranged at substantially the same position as that of the subject, as a measurement area of the gloss intensity distribution based on surface light source position information indicating the position of the surface light source and image capturing position information indicating the position of the image capturing apparatus that captures an image of the subject. Further, based on the surface light source position information, the image capturing position information, and pixel values of the captured image data, the gloss intensity distribution image data in the measurement area is generated.

17 Claims, 16 Drawing Sheets

(56) References Cited

U.S. PATENT DOCUMENTS

2012/0113443 A1* 5/2012 Itoh ................... H04N 1/4095
 358/1.9
2017/0205291 A1* 7/2017 Shimada ................ G01J 9/00

* cited by examiner

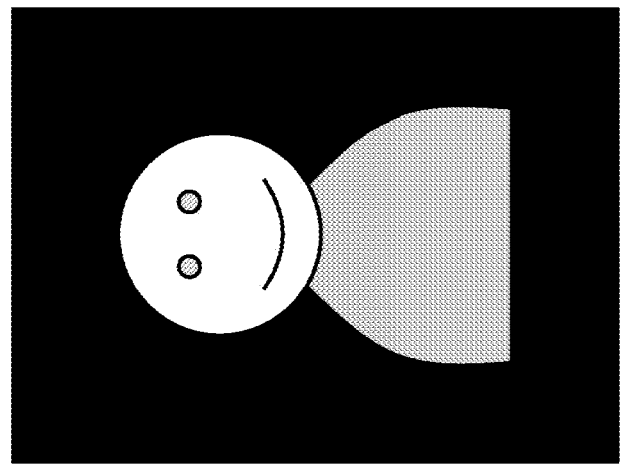
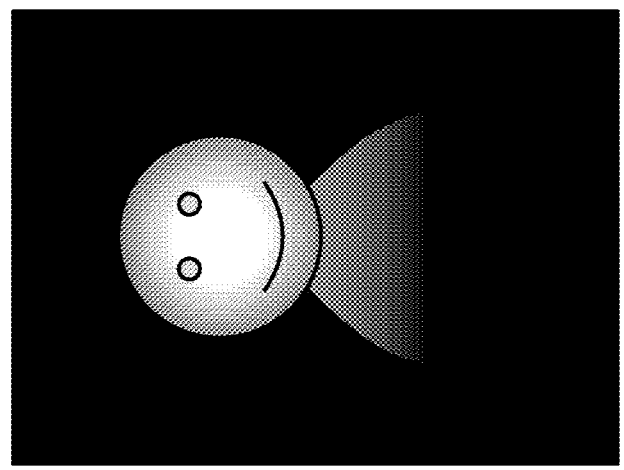
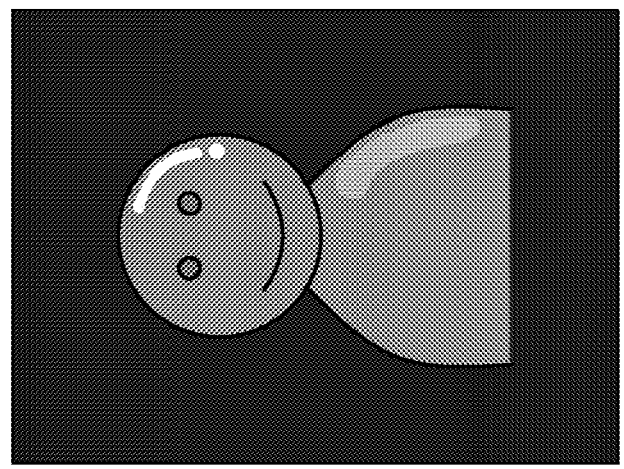
FIG. 11C
FIG. 11B
FIG. 11A

IMAGE PROCESSING APPARATUS, IMAGE PROCESSING METHOD, AND STORAGE MEDIUM

BACKGROUND OF THE INVENTION

Field of the Invention

The present invention relates to image processing to acquire a gloss intensity distribution of a subject from captured image data obtained by capturing an image of the subject having concavity/convexity.

Description of the Related Art

In recent years, the technique to acquire information other than color information from a subject having concavity/convexity is spreading. Information acquired from a subject having concavity/convexity is wide-ranging and includes information indicating a distance from an image capturing position to a subject, information indicating the shape of concavity/convexity of a subject, information indicating reflection characteristics of a subject and the like. In the case where information indicating reflection characteristics from a subject having concavity/convexity, it is necessary to adjust the arrangement of a light source and a light-receiving element in order to acquire a two-dimensional distribution of reflected light intensity (hereinafter, described as "gloss intensity distribution") because the specular reflection direction changes.

The more complicated the concavity/convexity shape, the more complicatedly the specular reflection direction changes, and therefore, it was difficult to adjust the arrangement of a light source and a light-receiving element in order to acquire a high-accuracy gloss intensity distribution. Japanese Patent Laid-Open No. 2005-227197 has disclosed a reflected light measuring method of acquiring a gloss intensity distribution of a subject while reducing a measurement error accompanying a change in the specular reflection direction by irradiating a subject having a concavity/convexity shape by using a surface light source.

SUMMARY OF THE INVENTION

The image processing apparatus of the present invention is an image processing apparatus that generates gloss intensity distribution image data indicating a gloss intensity distribution based on captured image data obtained by capturing an image of a subject having concavity/convexity irradiated by a surface light source, and includes: a setting unit configured to set an area, in which specularly reflected light from the surface light source enters a planar mirror and which is the same size as or smaller than that of an area captured by an image capturing apparatus in a case where the planar mirror is arranged at substantially the same position as that of the subject, as a measurement area of the gloss intensity distribution based on surface light source position information indicating the position of the surface light source and image capturing position information indicating the position of the image capturing apparatus that captures an image of the subject; and a generation unit configured to generate the gloss intensity distribution image data in the measurement area based on the surface light source position information, the image capturing position information, and pixel values of the captured image data.

Further features of the present invention will become apparent from the following description of exemplary embodiments with reference to the attached drawings.

BRIEF DESCRIPTION OF THE DRAWINGS

FIG. 11A is an image diagram of a subject having concavity/convexity;

FIG. 11B is an image diagram of a gloss intensity distribution image acquired by using a point light source;

FIG. 11C is an image diagram of a gloss intensity distribution image acquired by using a surface light source arranged in the vicinity;

DESCRIPTION OF THE EMBODIMENTS

With the reflected light measuring method described in Japanese Patent Laid-Open No. 2005-227197, reflected light from a subject is measured by using a special optical system called a telecentric optical system, and therefore, it is difficult to increase the size of the surface light source or to arrange the surface light source in the vicinity of a subject. That is, it is not possible to widen the area of irradiation using the surface light source in order to measure a gloss intensity distribution. Because of this, a very long time is required to acquire information indicating a gloss intensity distribution from a subject having concavity/convexity.

First Embodiment

In the following, embodiments for embodying the present invention are explained with reference to the drawings. However, components described in these embodiments are merely exemplary and are not intended to limit the scope of the present invention to those.

Figure 1:
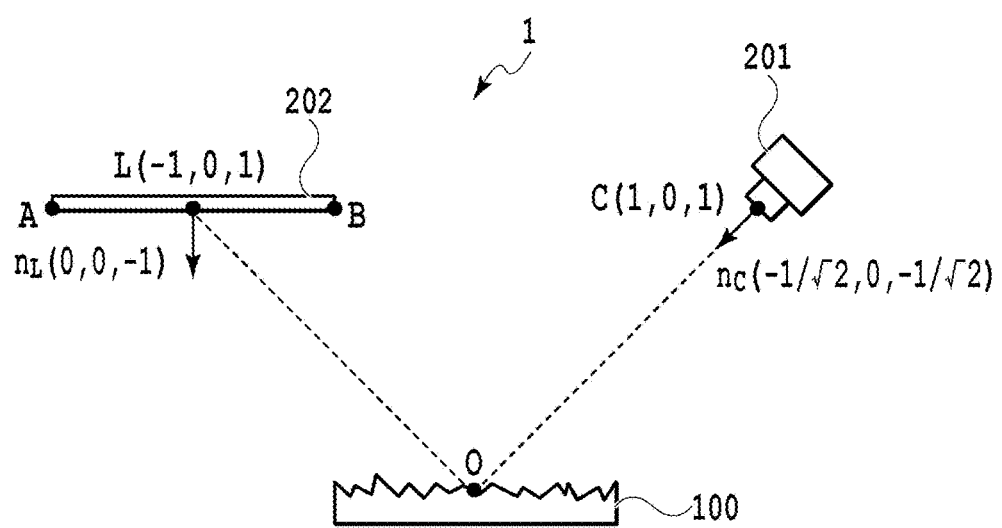
FIG. 1 is an outline diagram of an image processing system in a first embodiment.

FIG. 1 is an outline diagram of an image processing system 1 of the present embodiment. An oil painting having concavity/convexity formed by touches of a brush at the time of attaching color materials and a gloss due to the varnish applied onto the surface of the concavity/convexity as shown in FIG. 1 is taken to be a subject 100. In the present embodiment, a gloss intensity distribution is acquired from the subject 100 such as this. In the image processing system 1 shown in FIG. 1, the center on the substantially flat plane of the surface of the subject (oil painting) 100 is taken to be O. In the three-dimensional space coordinate system with O as the origin, an image capturing apparatus 201 that captures an image of the object 100 is arranged at a point C and a surface light source 202 having a size of a length of 1 and a width of 1 is arranged at a point L. Further, the image capturing apparatus 201 is arranged so as to face toward the direction of a vector $n_C=(-1/\sqrt{2}, 0, -1/\sqrt{2})$ indicating the direction of the optical axis. The surface light source 202 is arranged so as to face toward the direction of a vector $n_L=(0, 0, -1)$ indicating the direction of the plane normal line. In the present embodiment, the surface light source 202 includes a liquid crystal display that displays a white screen. The luminance of light emitted from the white screen of the liquid crystal display is uniform within the screen and the light is diffused light that diffuses isotropically.

Figure 2:
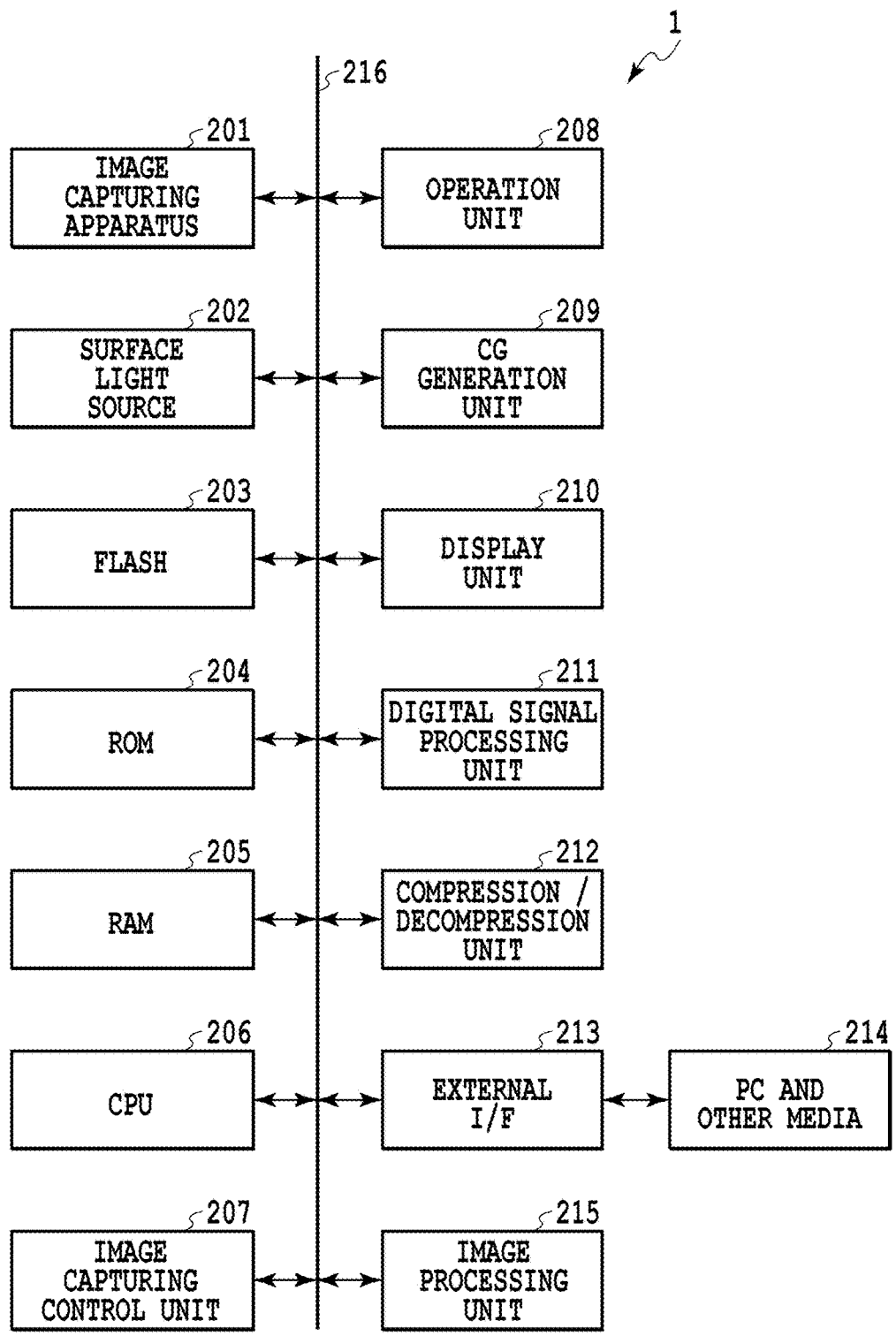
FIG. 2 is a hardware configuration diagram of the image processing system in the first embodiment.

FIG. 2 is a hardware configuration diagram of the image processing system 1 in the present embodiment. The image capturing apparatus 201 includes a lens, an aperture stop, a shutter, an optical low-pass filter, a color filter, and a sensor such as a CMOS sensor and a CCD sensor. The image capturing apparatus 201 detects the amount of light of a subject, performs A/D conversion for the detected amount of light, and outputs digital data to a bus 216, which is a data transfer path. The surface light source 202 and a flash 203 irradiate the subject 100 with light. A ROM 204 and a RAM 205 provide programs, data, a work area and the like necessary for image capturing and image processing to a CPU 206. The CPU 206 executes programs stored in the ROM 204 and the RAM 205 by using the RAM 205 as a work memory and controls each function block via the bus 216. By the CPU 206 controlling each function block, various kinds of processing, to be described later, are performed. An image capturing control unit 207 performs control of the image capturing system specified by the CPU 206, such as focusing, shutter opening, and aperture stop adjustment. An operation unit 208 includes a button, a mode dial and the like and receives instructions input by a user via those. A CG generation unit 209 generates characters, graphics and the like by CG (Computer Graphics). As a display unit 210, generally, a liquid crystal display is used widely and the display unit 210 displays images and characters received from the CG generation unit 209, a digital signal processing unit 211, and an image processing unit 215, to be described later. Further, the display unit 210 may have a touch screen function and in this case, it is possible to handle user instructions whose input has been received via the display unit 210 as an input to the operation unit 208. The digital signal processing unit 211 performs white balance processing, gamma processing, noise reduction processing and the like for the digital data received from the image capturing apparatus 201 and generates digital image data. A compression/decompression unit 212 converts digital image data generated by the digital signal processing unit 211 into a predetermined file format, such as jpeg and mpeg. An external interface 213 (hereinafter, described as "I/F") is an interface to connect a PC and other media 214 (e.g., hard disk, memory card, CF card, SD card, USB memory and the like) and the image processing system 1. The image processing unit 215 generates new image data by using the digital data received from the image capturing apparatus 201 or the digital image data generated by the digital signal processing unit 211 and outputs the generated new image data to the bus 216. The components in the image processing system 1 exist other than those described above, but they are not the main purpose of the present embodiment, and therefore, explanation is omitted.

Figure 3:
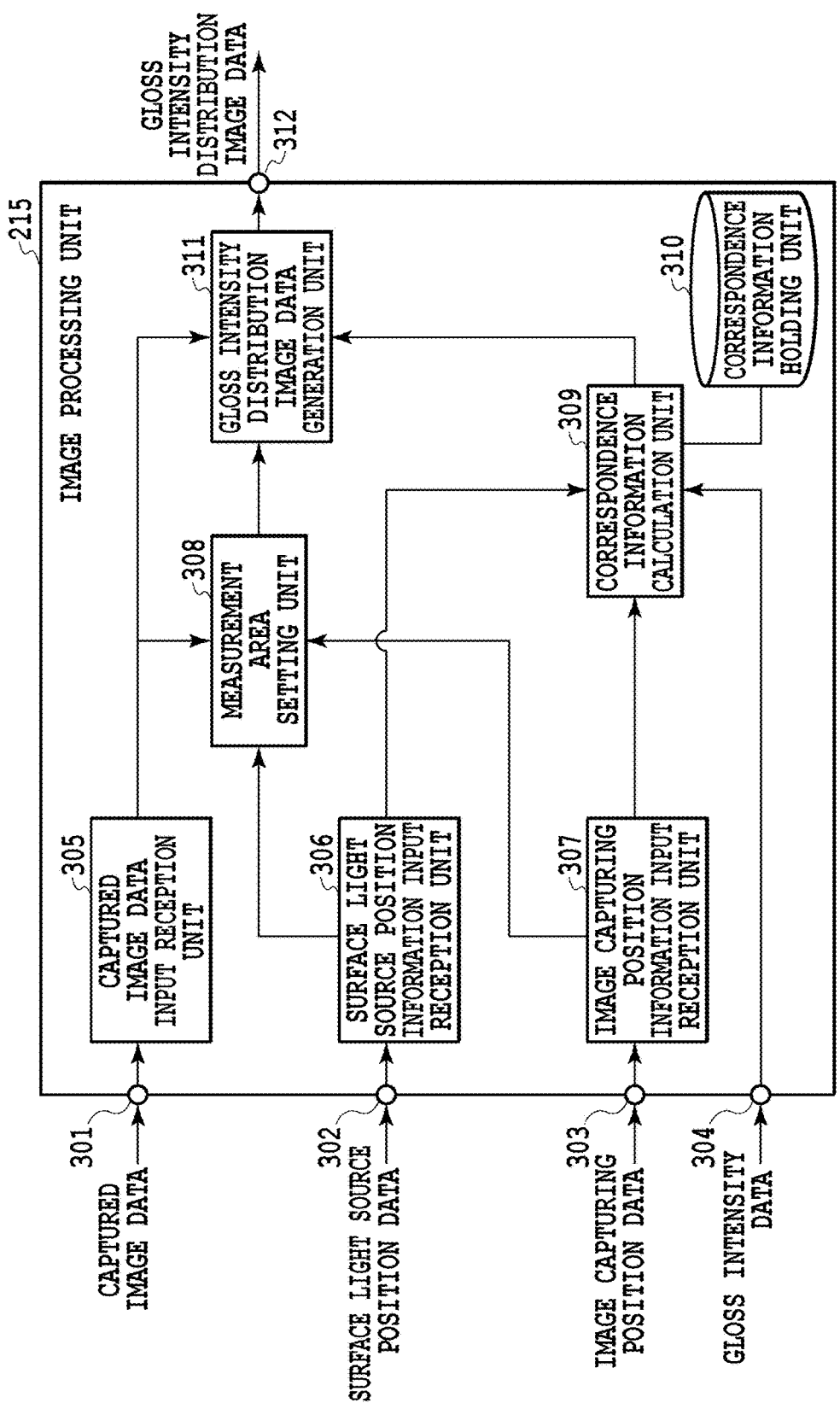
FIG. 3 is a software function configuration diagram of an image processing unit in the first embodiment.

FIG. 3 is a block diagram showing a software function configuration of the image processing unit 215 in the present embodiment. A processing procedure that is performed by image processing application software of the present embodiment based on instructions from the CPU 206 is explained with reference to FIG. 3.

A captured image data input reception unit 305 receives an input of data of a captured image captured by the image capturing apparatus 201 under the surface light source 202 via an input terminal 301. The captured image data whose input has been received is further output to a measurement area setting unit 308 and a gloss intensity distribution image data generation unit 311. A surface light source position information input reception unit 306 receives an input of data and a signal indicating the surface light source position information at the time of image capturing via an input terminal 302. The surface light source position information whose input has been received is further output to the measurement area setting unit 308 and a correspondence information calculation unit 309. An image capturing position information input reception unit 307 receives an input of data and a signal indicating the position information on the image capturing apparatus 201 via an input terminal 303. The image capturing position information whose input has been received is further output to the measurement area setting unit 308 and the correspondence information calculation unit 309.

The measurement area setting unit 308 sets a measurement area that is a target of measurement of a gloss intensity distribution of the subject 100 from the captured image data, the surface light source position information, and the image capturing position information. The measurement area information indicating the measurement area is output to the gloss intensity distribution image data generation unit 311.

The correspondence information calculation unit 309 calculates information indicating correspondence relationship between pixel value and gloss intensity in which pixel values and reference gloss intensities are associated with each other under various image capturing conditions from the surface light source position information, the image capturing position information, and the reference gloss intensity and stores the information indicating correspondence relationship between pixel value and gloss intensity in a correspondence information holding unit 310. Further, in response to a request from the gloss intensity distribution image data generation unit 311, the information indicating correspondence relationship between pixel value and gloss intensity is output to the gloss intensity distribution image data generation unit 311 as data or a signal indicating the information. The gloss intensity distribution image data generation unit 311 generates gloss intensity distribution image data indicating a gloss intensity distribution from the captured image data, the measurement area information, and the information indicating correspondence relationship between pixel value and gloss intensity. The generated gloss intensity distribution image data is output from an output terminal 312.

(Operation of Image Processing Unit)

Figure 4:
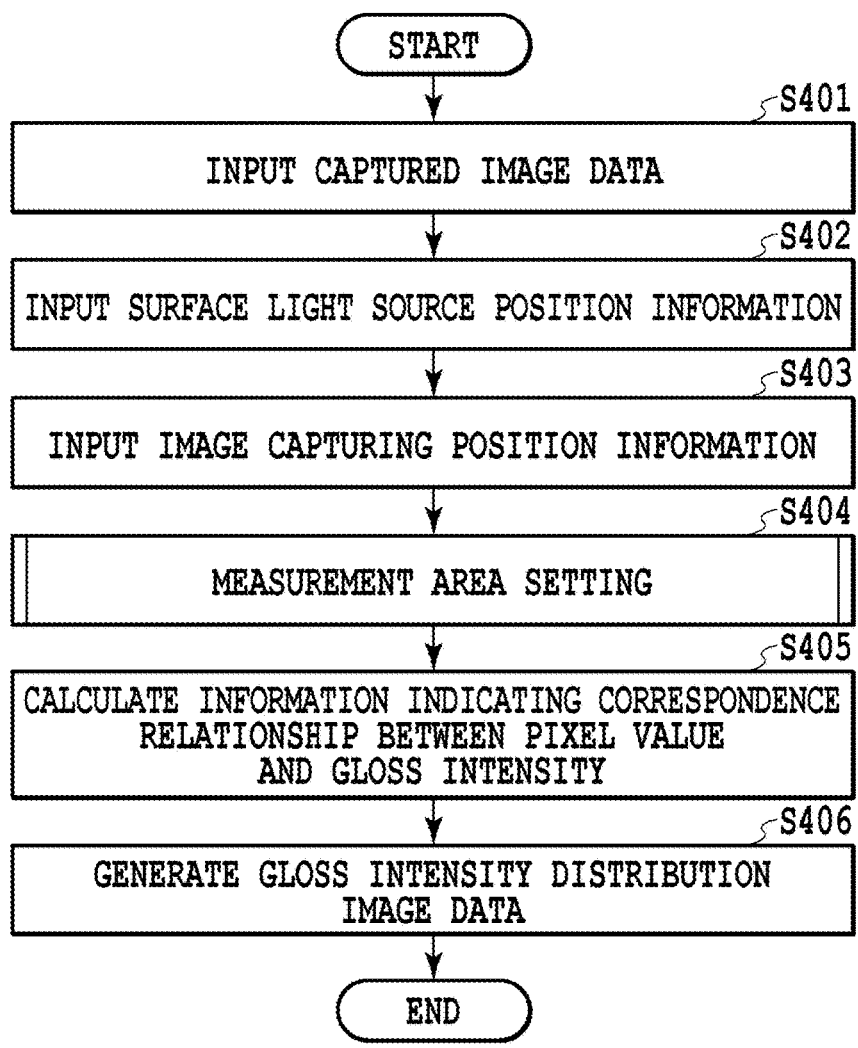
FIG. 4 is a flowchart showing an image processing procedure in the first embodiment.

Next, the processing procedure in the image processing unit 215 of the present embodiment is explained with reference to a flowchart in FIG. 4. The processing by the flowchart shown in FIG. 4 is performed by the CPU 206 loading the program code stored in the ROM 204 onto the RAM 205 and executing the program code. This is also true with the processing in FIG. 5. Symbol S described hereinafter means that the step is a step in the flowchart.

At S401, the captured image data input reception unit 305 receives an input of data of a captured image captured by the image capturing apparatus 201 under the surface light source 202. The captured image data whose input has been received is stored in the storage area, such as the RAM 205.

At S402, the surface light source position information input reception unit 306 receives an input of the surface light source position information at the time of image capturing. In the image processing system 1 of the present embodiment, as shown in FIG. 1, at the position of the point L (−1, 0, 1), the liquid crystal display having a size of a length of 1 and a width of 1 is arranged so as to face toward the direction of $n_L=(1, 0, −1)$. The surface light source position information whose input has been received is stored in the storage area, such as the RAM 205.

At S403, the image capturing position information input reception unit 307 receives an input of the position information on the image capturing apparatus 201. In the image processing system 1 of the present embodiment, as shown in FIG. 1, at the position of the point C (1, 0, 1), the image capturing apparatus 201 is arranged so as to face toward the direction of $n_C=(−1/\sqrt{2}, 0, −1/\sqrt{2})$. The image capturing position information whose input has been received is stored in the storage area, such as the RAM 205.

At S404, the measurement area setting unit 308 sets a measurement area that is a target of measurement of a gloss intensity distribution of the subject 100 from the captured image data, the surface light source position information, and the image capturing position information. Details of the processing to set a measurement area will be described later with reference to FIG. 5. The measurement area information indicating the measurement area is stored in the storage area, such as the RAM 205.

At S405, the correspondence information calculation unit 309 calculates information indicating correspondence relationship between pixel value and gloss intensity under the image capturing condition specified by the surface light source position information and the image capturing position information. Here, a method by which the correspondence information calculation unit 309 acquires information indicating correspondence relationship between pixel value and gloss intensity under various image capturing conditions is explained.

In the present embodiment, to the entire surface of an oil painting used as the subject 100, varnish is applied. Because of this, it is possible to regard that the refractive index is fixed across the entire surface of the oil painting. In the present embodiment, it is assumed that, for example, a refractive index $\eta=1.3$ across the entire surface of the oil painting. The refractive index of the oil painting surface is fixed, and therefore, it is possible to consider that the reflection characteristics of the oil painting surface caused by the shine of varnish depend on the surface roughness of the oil painting surface.

In the present embodiment, in order to represent such the reflection characteristics as described above, a BRDF (Bidirectional Reflectance Distribution Function) model is used. In the BRDF model expressed by expression (1), a Cook-Torrance model representing the surface roughness by a distribution of minute plane normal lines directed in various directions is further used.

$$BRDF_{Cook-Torrance} = \frac{DFG}{n_C \cdot N} \quad \text{expression (1)}$$

In expression (1), D is a Beckmann distribution indicating a distribution of minute plane normal lines representing the surface roughness. The Beckmann distribution D is expressed by expression (2) below.

$$D = D(\theta_{NH}, m) = \frac{1}{4m^2\cos^4\theta_{NH}} e^{-\left(\frac{\tan\theta_{NH}}{m}\right)^2} \quad \text{expression (2)}$$

Figure 6A:
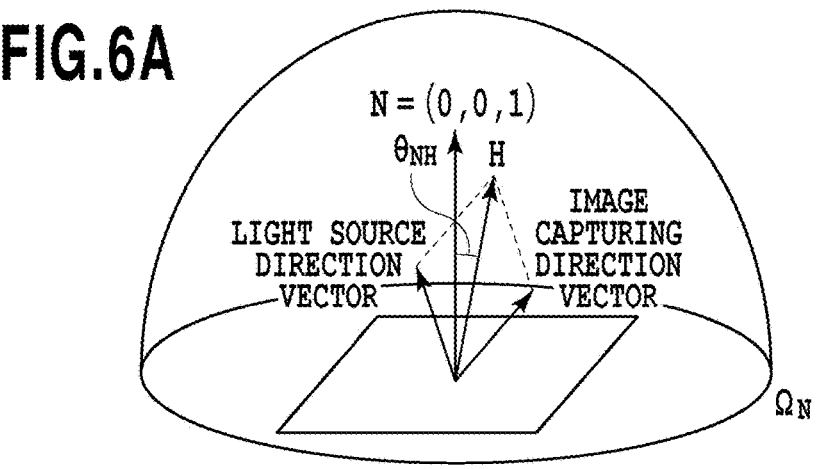
FIG. 6A is a schematic diagram explaining $\theta_{NH}$, a half vector H, and a plane normal line direction vector N.

In expression (2), m is a parameter indicating the surface roughness and indicates an average inclination of the minute planes. Here, $\theta_{NH}$ is an angle formed by a half vector H, which is a resultant vector of a light source direction vector and an image capturing direction vector, and a macro plane normal line direction vector N of the distribution of minute plane normal lines directed in various directions. A schematic diagram explaining $\theta_{NH}$, the half vector H, and the plane normal line direction vector N is shown in FIG. 6A. In the present embodiment, the correspondence information calculation unit 309 sets N=(0, 0, 1) by regarding the subject 100 as being a substantially flat plane at the time of acquiring information indicating correspondence relationship between pixel value and gloss intensity.

As expressed by expression (3) below, the Beckmann distribution D is normalized so that 1 is obtained in the case where the Beckmann distribution D is integrated in an upper hemispheric area $\Omega_N$ with the direction of the macro plane normal line direction vector N being taken to be the direction toward the zenith.

$$\int_{\Omega_N} D(\theta_{NH}, m)(N \cdot \theta_{NH}) d\theta_{NH} = 1 \quad \text{expression (3)}$$

Figure 6B:
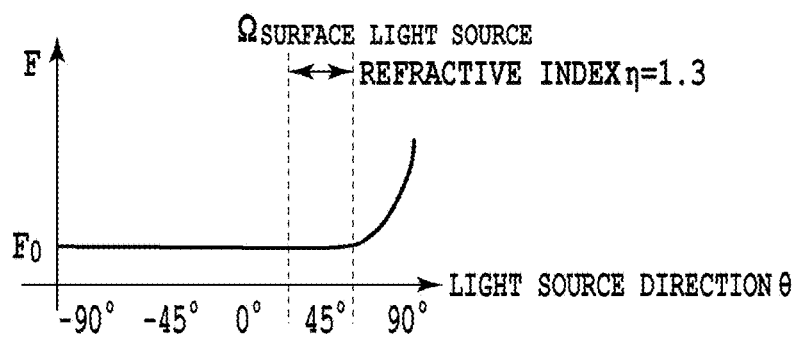
FIG. 6B is a graph explaining a relationship in which a Fresnel term F becomes a fixed value $F_0$.

In expression (1), F is the Fresnel term representing the reflectance in the case where light enters the interface between substances with different refractive indexes. As described previously, the subject 100 of the present embodiment is an oil painting to the entire surface of which, varnish is applied, and the refractive index η is regarded as being 1.3 across the entire surface of the oil painting. Because of this, under the image capturing condition of the present embodiment, the intensity of the Fresnel reflection in an angle area $\Omega_{surface\ light\ source}$ entered by the light from the surface light source 202 is fixed and it is possible to regard the Fresnel term F as being a fixed value $F_0$. Here, the angle area entered by the light from the surface light source is an area defined by the angle formed by light source direction vectors from the origin O to the left and right ends A and B of the surface light source L in the case where explanation is given by taking FIG. 1 as an example. Hereinafter, in the present embodiment, the angle area entered by the light from the surface light source is described as the angle area $\Omega_{surface\ light\ source}$. A schematic diagram explaining a relationship by which the Fresnel term F corresponding to the angle area $\Omega_{surface\ light\ source}$ becomes the fixed value F0 under the image capturing condition of the present embodiment is shown in FIG. 6B.

Figure 6C:
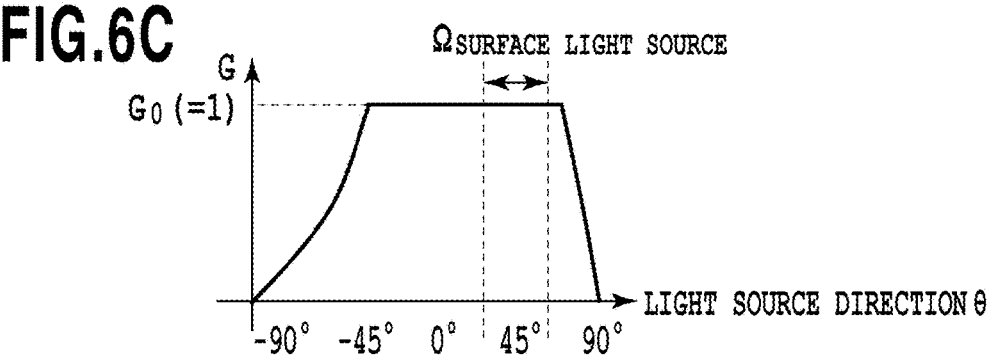
FIG. 6C is a graph explaining a relationship in which a geometric attenuation term G becomes a fixed value $G_0$.

In expression (1), G is a geometric attenuation term indicating attenuation of the reflected light due to self light shielding/self shading caused by the concavity/convexity portion of a minute plane. The geometric attenuation term has characteristics that the geometric attenuation term indicates a fixed value in the case where a light source direction θ is within a predetermined angle range. In the present embodiment, on the premise that the angle area $\Omega_{surface\ light\ source}$ entered by the light from the surface light source 202 is within the above-described predetermined angle range, it is possible to regard the geometric attenuation term G as being a fixed value $G_0$ ($G_0=1$). A schematic diagram explaining a relationship by which the geometric attenuation term G corresponding to the angle area $\Omega_{surface\ light\ source}$ becomes the fixed value $G_0$ ($G_0=1$) under the image capturing condition of the present embodiment is shown in FIG. 6C.

In expression (1), $n_c$ is the vector indicating the direction of the image capturing apparatus 201 having received the input at S403, and in the present embodiment, $n_c=(-1/\sqrt{2}, 0, -1/\sqrt{2})$. The vector $n_c$ such as this that indicates the direction of the image capturing apparatus 201 can be said to be one aspect of image capturing position information. As described above, in the present embodiment, the reflectance characteristics of the subject 100 are acquired based on the BRDF model, but any model may be used as long as the model can represent the reflectance characteristics of the subject 100 in accordance with the surface roughness.

As explained above, in the present embodiment, it is possible to regard the Fresnel term F, the geometric attenuation term G, the image capturing apparatus direction vector $n_c$, and the macro plane normal line direction vector as being fixed. Consequently, it is possible to represent the pixel value for each pixel position in the data of the captured image captured under the surface light source by the value (BRDF integrated value) obtained by integrating BRDF in the angle area entered by the light from the surface light source and further, the BRDF integrated value is proportional to the value obtained by integrating the Beckmann distribution D. The value obtained by integrating the Beckmann distribution D in the angle area $\Omega_{surface\ light\ source}$ is expressed by expression (4) below.

$$\int_{\Omega_{surface\ light\ source}} BRDF_{Cook-Torrance} d\theta_{NH} \cong \frac{F_0 G_0}{n_C \cdot N} \int_{\Omega_{surface\ light\ source}} D(\theta_{NH}, m) d\theta_{NH} \qquad \text{expression (4)}$$

As described above, the Beckmann distribution D is normalized so that 1 is obtained in the case where the Beckmann distribution D is integrated in the upper hemispheric area $\Omega_N$ with the direction of the macro plane normal line direction vector N being taken to be the direction toward the zenith. In the present embodiment, the surface light source is used, and therefore, the angle area $\Omega_{surface\ light\ source}$ entered by the light from the surface light source is smaller than the upper hemispheric area $\Omega_N$ without exception. At this time, in the case where the surface smooth degree of the subject 100 is high, the integrated value of the Beckmann distribution D in the angle area $\Omega_{surface\ light\ source}$ becomes close to 1. On the other hand, in the case where the surface smooth degree of the subject 100 is low, the integrated value of the Beckmann distribution D in the angle area $\Omega_{surface\ light\ source}$ becomes a value smaller than that in the case where the surface smoothness degree of the subject 100 is high. A relationship between the integrated values of the Beckmann distribution D is expressed by expression (5) below.

$$\int_{\Omega_{surface\ light\ source}} D(\theta_{NH}, m_B) d\theta_{NH} < \qquad \text{expression (5)}$$
$$\int_{\Omega_{surface\ light\ source}} D(\theta_{NH}, m_A) d\theta_{NH}$$

In expression (5), D ($\theta_{NH}$, $m_A$) indicates the Beckmann distribution in the case where the surface smoothness degree of the subject 100 is high. On the other hand, in expression (5) D ($\theta_{NH}$, $m_B$) indicates the Beckmann distribution in the case where the surface smoothness degree of the subject 100 is low (e.g., the surface is coarse).

Here, as described above, in the present embodiment, it is possible to regard the Fresnel term $F_0$, the geometric attenuation term $G_0$, the camera direction $n_c$, and the macro plane normal line direction N as being fixed, respectively. Because of this, it is possible to represent a gloss intensity $I_{MAX}$ corresponding to the pixel position of the captured image data by BRDF in the case where the Beckmann distribution D becomes the maximum. A relationship between the gloss intensity $I_{MAX}$ and the maximum value of the Beckmann distribution D is expressed by expression (6) below.

$$I_{MAX} = MAX[BRDF_{Cook-Torrance}] \cong \frac{F_0 G_0}{n_C \cdot N} D_{MAX}(\theta_{NH}, m) \qquad \text{expression (6)}$$

$D_{MAX}$ ($\theta_{NH}$, m) indicates the maximum value of the Beckmann distribution D in the case where the surface roughness is m. As described previously, the maximum value $D_{MAX}$ ($\theta_{NH}$, m) of the Beckmann distribution D becomes a larger value for the higher surface smoothness degree of the subject 100. The maximum value $D_{MAX}$ ($\theta_{NH}$, m) of the Beckmann distribution D in accordance with the surface smoothness degree of the subject 100 is expressed by expression (7) below.

$$D_{MAX}(\theta_{NH}, m_B) < D_{MAX}(\theta_{NH}, m_A): \qquad \text{expression (7)}$$

Figure 7:
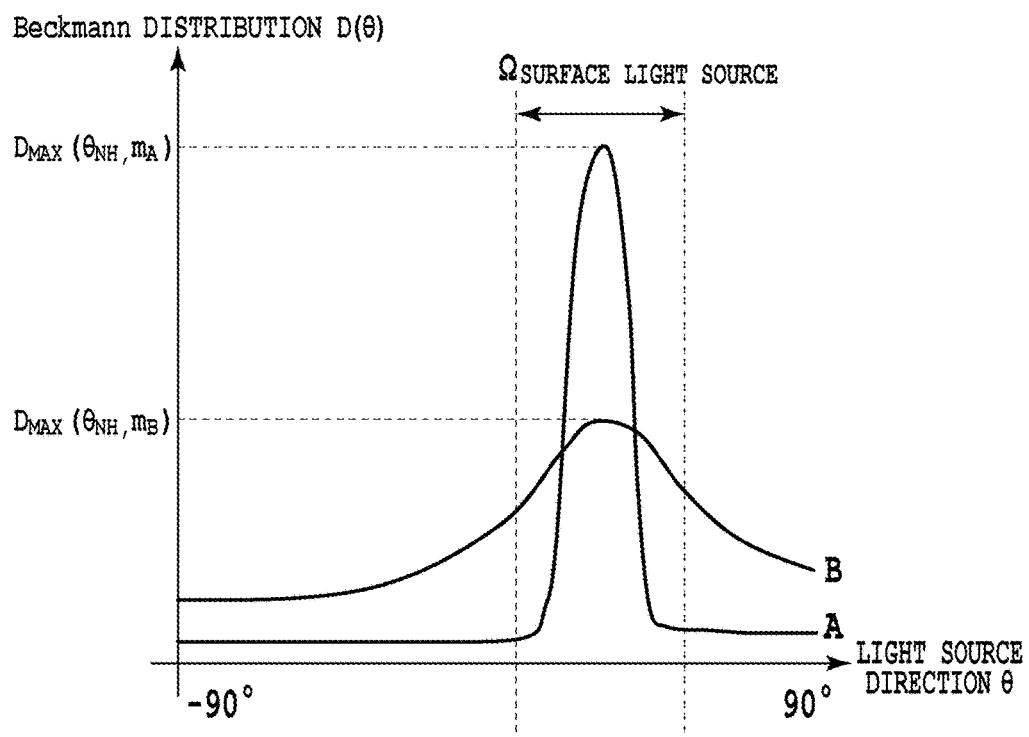
FIG. 7 is a graph showing a maximum value of a Beckmann distribution D in the first embodiment.

As shown in FIG. 7, $D_{MAX}$ ($\theta_{NH}$, $m_A$) corresponds to a curve A and indicates the maximum value of the Beckmann distribution D in the case where the surface smoothness degree of the subject 100 is high. On the other hand, $D_{MAX}$ ($\theta_{NH}$, $m_B$) corresponds to a curve B and indicates the maximum value of the Beckmann distribution D in the case where the surface smoothness degree of the subject 100 is low.

In the present embodiment, the information indicating correspondence relationship between pixel value and gloss intensity under the various image capturing conditions is calculated by a simulation by the correspondence information calculation unit 309 and stored in advance in the correspondence information holding unit 310. In the following, the calculation method of information indicating correspondence relationship between pixel value and gloss intensity by the correspondence information calculation unit 309 is explained.

In the present embodiment, it is possible for the correspondence information calculation unit 309 to calculate the information indicating correspondence relationship between pixel value and gloss intensity by using expressions (2) and (6) described above. As described previously, it is possible to regard the Fresnel term F, the geometric attenuation term G, the image capturing apparatus direction vector $n_c$, and the macro plane normal line direction vector N as being fixed under a certain image capturing condition. At this time, in expressions (2) and (6), $I_{MAX}$ and m are unknown variables. The correspondence information calculation unit 309 inputs a reference gloss intensity into the unknown variable $I_{MAX}$ and calculates the value of m corresponding to each value of $I_{MAX}$.

Subsequently, it is possible for the correspondence information calculation unit 309 to calculate the BRDF integrated value corresponding to the value of $I_{MAX}$ by inputting the calculated m into expressions (2) and (4). In the present embodiment, the correspondence information calculation unit 309 maps the BRDF integrated value corresponding to the value of $I_{MAX}$ to an 8-bit value (0 to 255). As described above, it is possible for the correspondence information calculation unit 309 to calculate the corresponding BRDF integrated value from the value (reference gloss intensity) of $I_{MAX}$ whose input has been received and the correspondence information calculation unit 309 stores the correspondence information in the correspondence information holding unit 310 as the information indicating correspondence relationship between pixel value and gloss intensity.

Figure 8A:
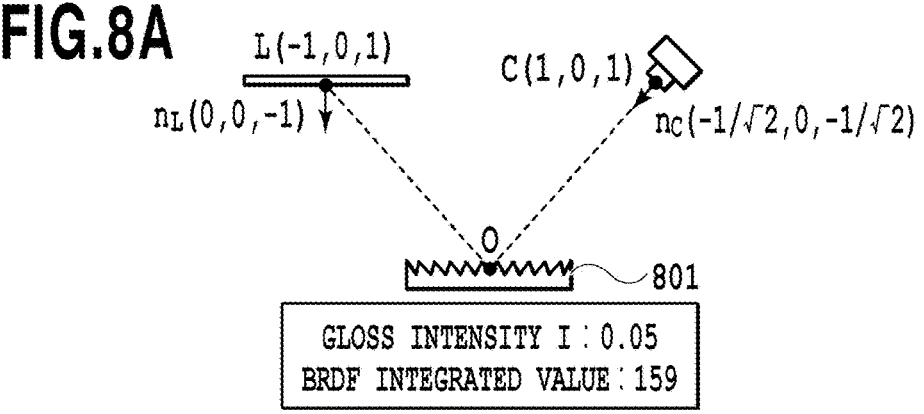
FIG. 8A to FIG. 8C are each a schematic diagram showing an example of a calculation method of information indicating correspondence relationship between pixel value and gloss intensity in the first embodiment.
Figure 8B:
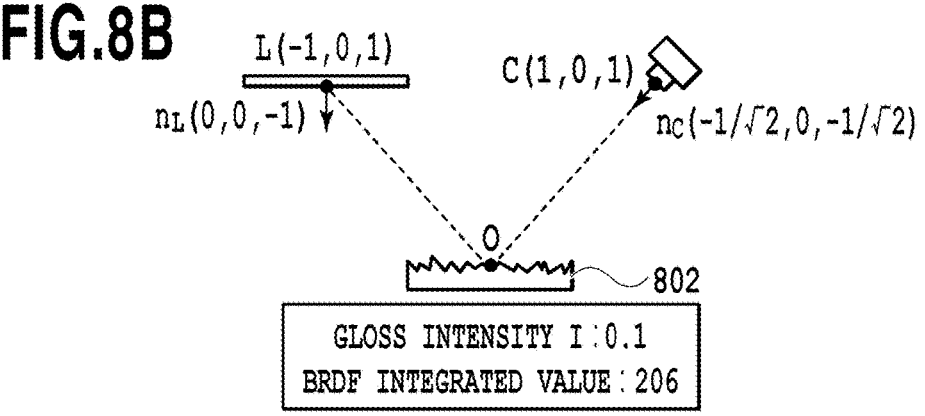
Figure 8C:
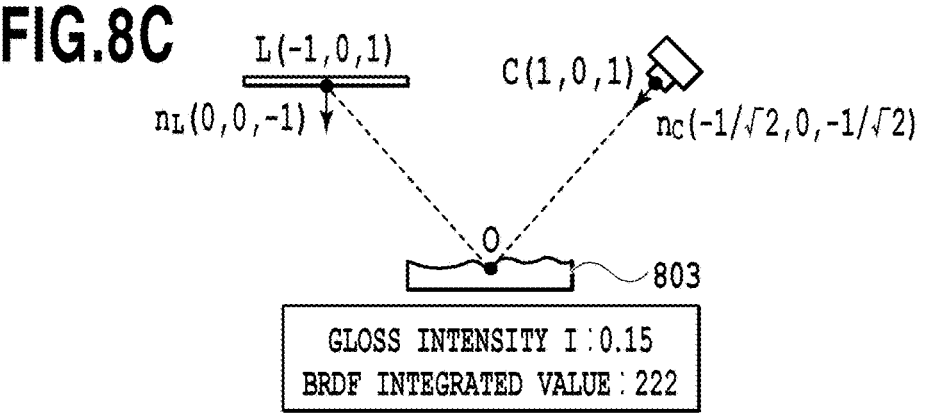

FIG. 8A to FIG. 8C are each a diagram showing an example in which information indicating correspondence relationship between pixel value and gloss intensity is calculated by a simulation under the image capturing condition shown in FIG. 1. In FIG. 8A to FIG. 8C, the correspondence information calculation unit 309 inputs values of 0 to 0.15 to $I_{MAX}$ and calculates the BRDF integrated values corresponding to $I_{MAX}$: 0 to 0.15, respectively. Reference numerals 801 to 803 indicate virtual samples having the gloss intensities $I_{MAX}$ of 0.05, 0.10, and 1.05, respectively. As explained above, it is possible for the correspondence information calculation unit 309 to obtain the BRDF integrated value corresponding to the value of $I_{MAX}$ by calculating the values of m corresponding to the gloss intensities $I_{MAX}$, respectively, and based on the calculated values of m. In the examples in FIG. 8A to FIG. 8C, the corresponding BRDF integrated values 159, 206, and 222 are calculated for the gloss intensities 0.05, 0.10, and 0.15, respectively.

Figure 9A:
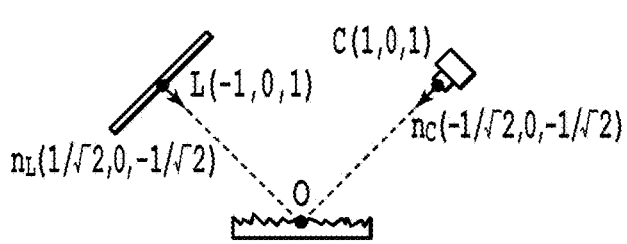
FIG. 9A to FIG. 9F are each a diagram showing an example of information indicating correspondence relationship between pixel value and gloss intensity under each image capturing condition in the first embodiment.
Figure 9D:
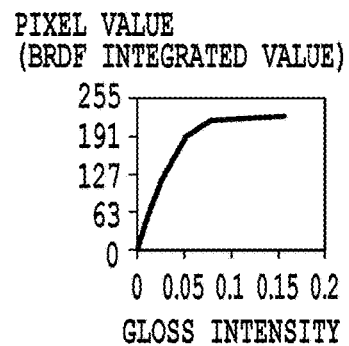
Figure 9B:
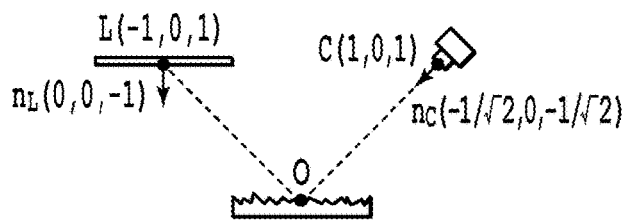
Figure 9E:
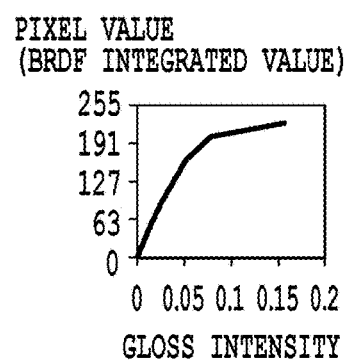
Figure 9C:
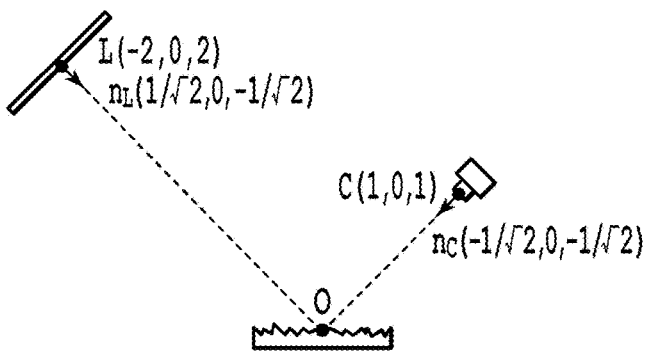
Figure 9F:
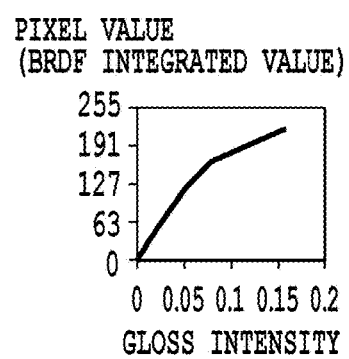

The calculation of the information indicating correspondence relationship between pixel value and gloss intensity by the simulation explained in FIG. 8A to FIG. 8C is performed for each image capturing condition. FIG. 9A to FIG. 9C are each a diagram showing an example of the different image capturing condition in the present embodiment and FIG. 9D to FIG. 9F are each a diagram showing an example of the information indicating correspondence relationship between pixel value and gloss intensity corresponding to FIG. 9A to FIG. 9C, respectively. Among these, the image capturing condition explained in FIG. 8A to FIG. 8C corresponds to FIG. 9B and the information indicating correspondence relationship between pixel value and gloss intensity explained in FIG. 8A to FIG. 8C corresponds to FIG. 9E, respectively. As described above, it is possible for the correspondence information calculation unit 309 of the present embodiment to calculate in advance the information indicating correspondence relationship between pixel value and gloss intensity for each image capturing condition by a simulation and to store the information indicating correspondence relationship between pixel value and gloss intensity in the correspondence information holding unit 310. The correspondence information calculation unit 309 selects the image capturing condition closest to a combination of the surface light source position information whose input has been received at S402 and the image capturing position information whose input has been received as S403. Then, in response to the request from the gloss intensity distribution image data generation unit 311, the correspondence information calculation unit 309 outputs the information indicating correspondence relationship between pixel value and gloss intensity corresponding to the selected image capturing condition.

In the present embodiment, the aspect is explained in which a desired value is input to $I_{MAX}$ that is an unknown variable and the corresponding BRDF value is calculated from each value of $I_{MAX}$, but it may also be possible to calculate information indicating correspondence relationship between pixel value and gloss intensity based on captured image data obtained by capturing an image of a measurement sample, such as gloss paper. In this case, by associating the pixel values of the captured image data obtained by capturing images a plurality of kinds of measurement sample whose gloss intensity is known with the corresponding gloss intensities, it is possible to acquire information indicating correspondence relationship between pixel value and gloss intensity. It is sufficient to perform the calculation of the information indicating correspondence relationship between pixel value and gloss intensity such as this for each image capturing condition. It is not necessary for the correspondence information calculation unit 309 to calculate the BRDF integrated values from all the gloss intensities and it may also be possible to calculate the BRDF integrated values for only part of the gloss intensities and to interpolate the BRDF integrated values by using the publicly known linear interpolation for the other BRDF integrated values.

Returning to the flowchart in FIG. 4 again, at S406, the gloss intensity distribution image data generation unit 311 generates gloss intensity distribution image data indicating a distribution of gloss intensities from the captured image data, the measurement area information, and the information indicating correspondence relationship between pixel value and gloss intensity. In the present embodiment, the gloss intensity distribution image data generation unit 311 generates gloss intensity distribution image data by converting the pixel value in the measurement area of the captured image data into the gloss intensity. The generated gloss intensity distribution image data is output from the output terminal 312 and stored in the storage area, such as the RAM 205. On the completion of the generation of the gloss intensity distribution image data (S406), the processing by this flowchart is terminated.

(Operation of Measurement Area Setting Unit)

Figure 5:
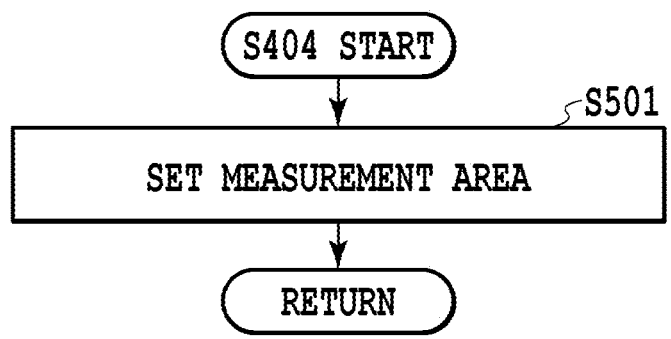
FIG. 5 is a flowchart showing the image processing procedure in the first embodiment.

Next, the detailed procedure of the measurement area setting processing at S404 is explained with reference to the flowchart in FIG. 5. At S501, the measurement area setting unit 308 sets a measurement area based on the surface light source position information and the image capturing position information. In the present embodiment, the area in which the specularly reflected light of the surface light source 202 enters the planar mirror and which is captured by the image capturing apparatus 201 in the case where the planar mirror is arranged at substantially the same position as that of the subject 100 is set as a measurement area.

Figures 10A, 10B:
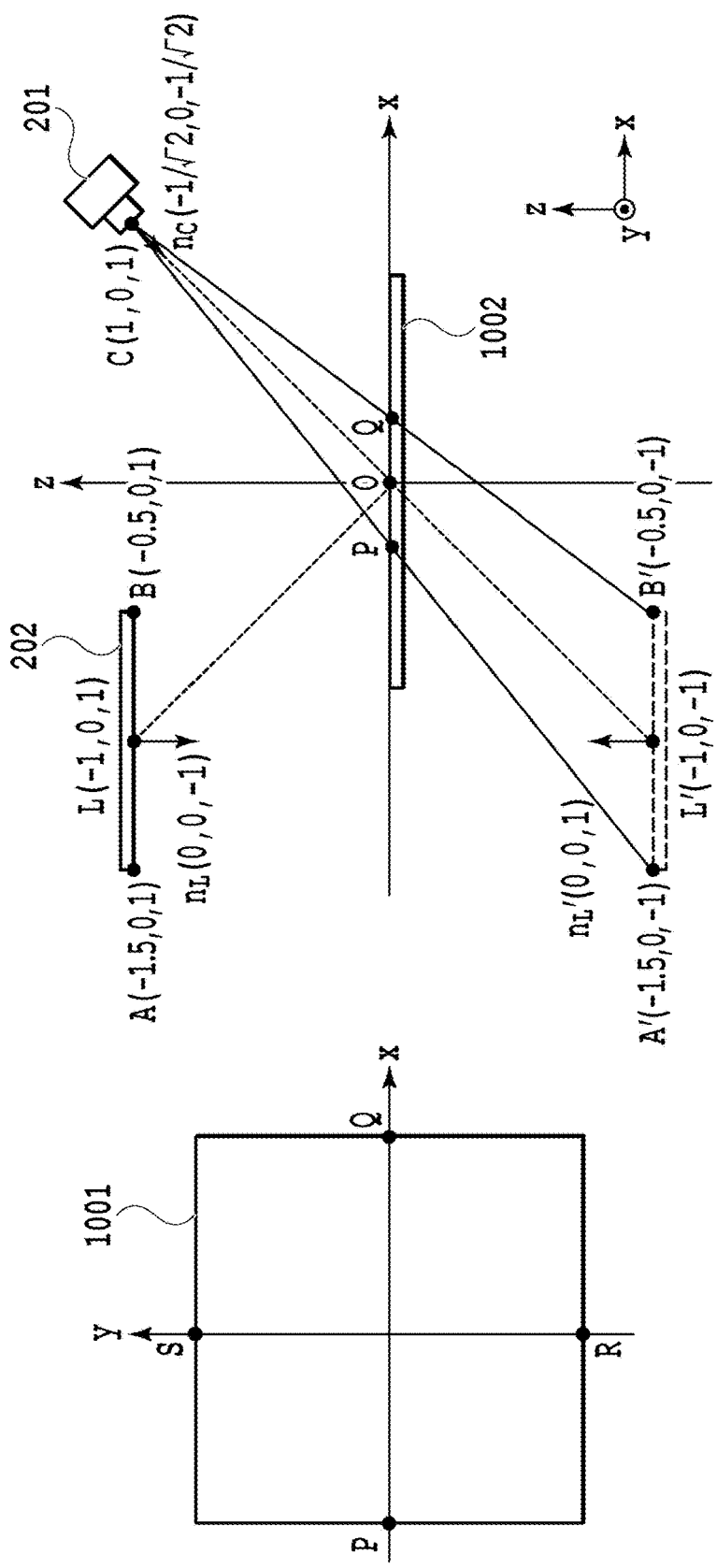
FIG. 10A and FIG. 10B are each a diagram showing a measurement area in the first embodiment.

The measurement area setting unit 308 calculates a range P<x<Q in the x-direction and a range R<y<S, in which the specularly reflected light of the surface light source 202 enters the planar mirror, in the xy-coordinate system shown in FIG. 10A and sets a rectangular area within the calculated xy range as a measurement area 1001.

FIG. 10B is a cross section diagram of the xz-plane at y=0 with the y-axis direction being taken to be a viewpoint. At the point L (−1, 0, 1), the surface light source L (surface light source 202) having a size of a length of 1 and a width of 1 is arranged and the left and right ends of the surface light source L are taken to be points A and B. A mirror image obtained by reflecting the surface light source L symmetrically with respect to the x-axis around the center of the surface of a planar mirror 1002 is taken to be L' and x-coordinates of intersections P and Q of straight lines connecting points A' and B', which are the left and right ends of the mirror image L', and a point C, which is the center of the camera lens, and the surface of the planar mirror 1002 are calculated in accordance with expressions (8) and (9) below.

$$(0\ 0\ 1)\cdot(tOA'+(1-t)OC)=0\ (0<t<1):\quad \text{expression (8)}$$

$$(0\ 0\ 1)\cdot(tOB'+(1-t)OC)=0\ (0<t<1):\quad \text{expression (9)}$$

OA', OB', and OC are position vectors of A', B', and C in the case where a point O is taken to be the origin. Here, t is a parameter that takes a value between 0 and 1 and indicates a position vector on segments A'C and B'C. Under the image capturing condition shown in FIG. 10A and FIG. 10B, t=0.5 is obtained both from expression (8) and from expression (9) and P=(−0.25, 0, 0) and Q=(0.25, 0, 0) are obtained. It is possible to perform the same calculation for the range R<y<S in the y-direction and the rectangular area within the calculated xy range is set as a measurement area. The measurement area setting unit 308 stores measurement area data indicating the set measurement area in the storage area, such as the RAM 205, and the processing returns to the flowchart in FIG. 4 again.

FIG. 11A is an image diagram of a subject having concavity/convexity. FIG. 11A shows an image diagram in which the reflection intensity of the face area in the subject is high, the reflection intensity of the trunk area is medium, and the reflection intensity of the background is low.

FIG. 11B is an image diagram of a gloss intensity distribution image acquired by using a point light source. The gloss intensity distribution image data indicating the gloss intensity distribution image in FIG. 11B is 8-bit grayscale image data. In the gloss intensity distribution image data in FIG. 11B, the specularly reflected light is observed only at the center of the face area, and therefore, the pixel value of the corresponding pixel area is as high as 255 and the pixel value decreases gradually as becoming more distant from the pixel area. In the case where gloss intensity distribution image data is acquired by using a point light source, the specularly reflected light is observed only at the center of the face area, and therefore, in order to acquire a gloss intensity distribution across the two-dimensional directions of the subject, it is necessary to repeatedly measure the specularly reflected light also in areas other than the center of the face area. As above, the conventional method of measuring the specularly reflected light by using a point light source is complicated and it requires much measurement time in order to acquire gloss intensity distribution image data.

FIG. 11C is an image diagram of a gloss intensity distribution image acquired by using a surface light source arranged in the vicinity. The gloss intensity distribution image data indicating the gloss intensity distribution image in FIG. 11C is also 8-bit grayscale image data. In the gloss intensity distribution image data in FIG. 11C, in the face area, the pixel value is 255 indicating a high gloss intensity, in the trunk area, the pixel value is 128 indicating a medium gloss intensity, and in the background area, the pixel value is 0 indicating a low gloss intensity. As above, in the present embodiment, by causing light from light sources in a number of dictions to enter a subject by using a surface light source arranged in the vicinity, it is possible to acquire gloss intensity distribution image data in a short time.

Further, in the present embodiment, information indicating correspondence relationship between pixel value and gloss intensity on an image captured under a surface light source is calculated on the assumption that a macro plane normal line N=(0, 0, 1), but it may also be possible to calculate information indicating correspondence relationship between pixel value and gloss intensity under an image capturing condition in which the plane normal line is inclined by the concavity/convexity of a subject. Furthermore, in the present embodiment, data indicating correspondence relationship between pixel value and gloss intensity at the center of a subject is calculated and the data indicating correspondence relationship between pixel value and gloss intensity within the measurement area is fixed. In a modification example, it may also be possible to use information indicating correspondence relationship between pixel value and gloss intensity different at each point within the measurement area, or it may also be possible to covert the pixel value into a gloss intensity by using the average value thereof.

In the present embodiment, the aspect is explained in which the information indicating correspondence relationship between pixel value and gloss intensity under various image capturing conditions is calculated in advance and stored in the correspondence information holding unit 310. In another embodiment, it may also be possible to calculate the information indicating correspondence relationship between pixel value and gloss intensity from the surface light source position information, the image capturing position information, and the gloss intensity each time an image of the subject 100 is captured.

Further, in the present embodiment, the surface light source is used whose luminance within the surface is uniform and which emits diffused light that spreads isotropically, but it may also be possible to use a surface light source having unevenness characteristics or light distribution characteristics within the surface.

Second Embodiment

In the first embodiment, explanation is given to the method of acquiring a gloss intensity distribution in a set measurement area by setting a range in which the specularly reflected light of the surface light source 202 enters a planar mirror in the case where the planar mirror is arranged at substantially the same position as that of the subject 100 as the measurement area. In the present embodiment, explanation is given to a method of efficiently acquiring a gloss intensity distribution by calculating a measurement area of the gloss intensity distribution within an angle range set by a user from a subject having concavity/convexity.

Figure 12:
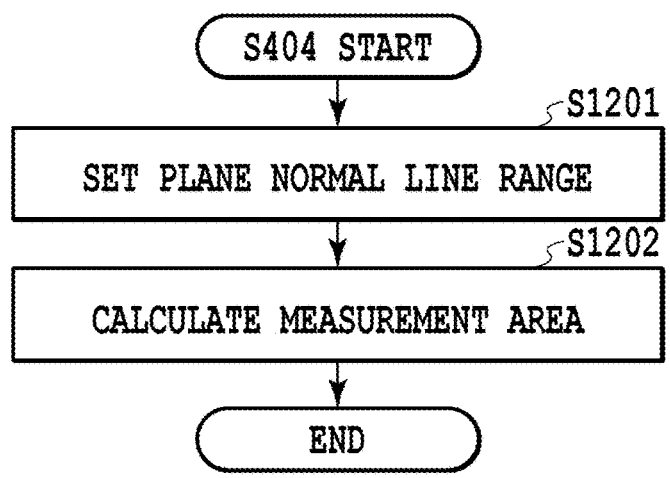
FIG. 12 is a flowchart showing an image processing procedure in a second embodiment.

FIG. 12 is a flowchart showing a processing procedure of the measurement area setting in the present embodiment. In the following, a detailed procedure of the measurement area setting at S404 is explained with reference to the flowchart in FIG. 12. Explanation of the portions in common to those of the first embodiment is simplified or omitted and in the following, points unique to the present embodiment are explained mainly.

At S1201, the measurement area setting unit 308 sets a plane normal line range from plane normal line range information indicating an angle range of a plane normal line of a subject whose input has been received from a user. In the present embodiment, the measurement area setting unit 308 sets an angle range between −5° and +5° whose input has been received from a user as a plane normal line range. The measurement area setting unit 308 stores the acquired plane normal line range information in the storage area, such as the RAM 205, as plane normal line range data.

At S1202, the measurement area setting unit 308 sets a measurement area from the surface light source position information, the image capturing position information, and the plane normal line range information. In the present embodiment, the area is set as a measurement area, in which the specularly reflected light of the surface light source 202 enters a mirror body and whose image is captured by the image capturing apparatus 201 in the case where the mirror body having a plane normal line in the plane normal line range between −5° and +5° is arranged at substantially the same position as that of the subject 100.

Figure 13B:
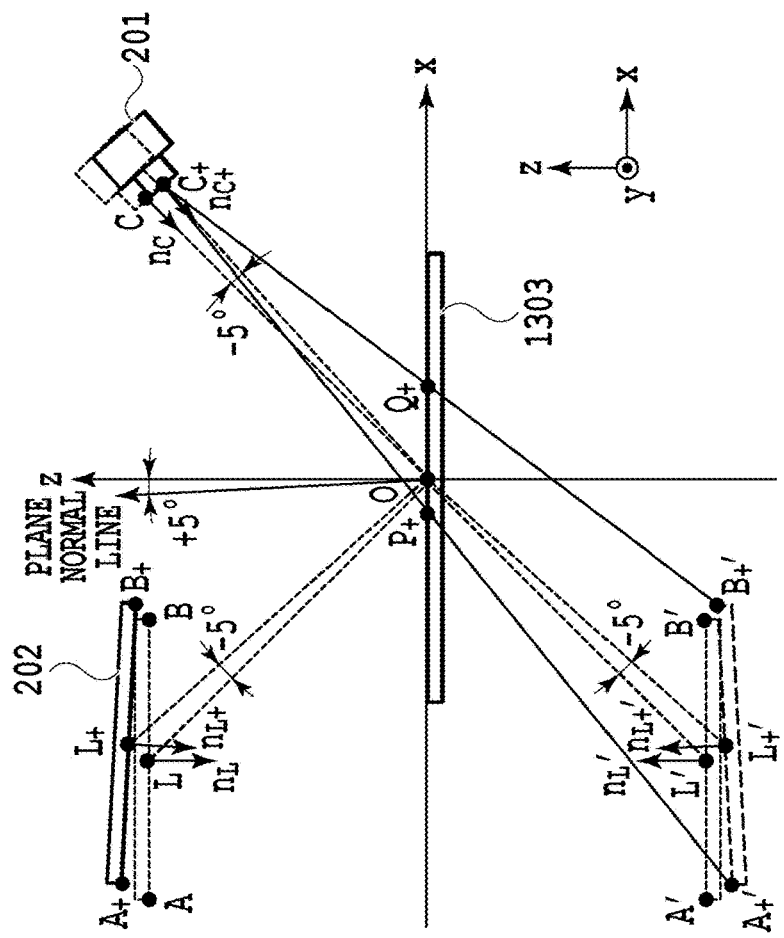
FIG. 13A and FIG. 13B are each a diagram showing a measurement area in the second embodiment.
Figure 13A:
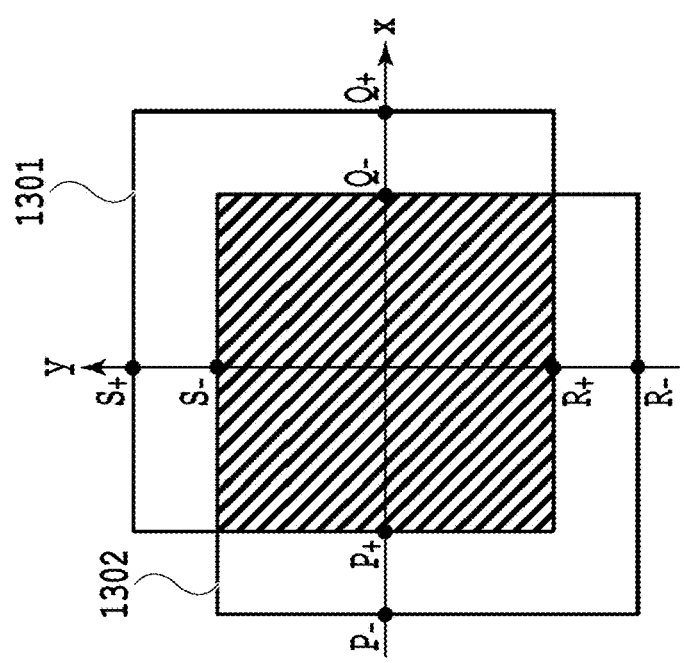

Specifically, in the xy-coordinate system shown in FIG. 13A, a range $P_+ < x < Q_+$ in the x-direction and a range $P_+ < y < Q_+$ in the y-direction in which the specularly reflected light of the surface light source enters the mirror body having the plane normal line +5° inclined are calculated. Similarly, a range $P_- < x < Q_-$ in the x-direction and a range $R_- < y < S_-$ in the y-direction in which the specularly reflected light of the surface light source enters the mirror body having the plane normal line −5° inclined are calculated. From calculated ranges (1301, 1302) in the x- and y-directions, the rectangular common area within the xy range calculated with +5° and −5° shown in the diagonally shaded portion in FIG. 13A is set as the measurement area.

First, the range $P_+ < x < Q_+$ in the x-direction in the case where a mirror body 1303 is inclined by +5° is calculated. FIG. 13B is a cross section diagram of the xz-plane at y=0 with the y-axis direction being taken to be a viewpoint. At the point L (−1, 0, 1), the surface light source L (surface light source 202) having a size of a length of 1 and a width of 1 is arranged and the left and right ends of the surface light source L are taken to be points A and B. Further, a mirror image of the surface light source L obtained by reflecting the surface light source L symmetrically with respect to the x-axis around the center of the surface of the mirror body 1303 is taken to be L' and the left and right ends of the mirror image L' are taken to be points A' and B'. At this time, the position L of the surface light source with the plane normal line +5° inclined as a reference is calculated in accordance with expression (10) below.)

$$OL_+ = Rot(0°, -5°) \cdot OL: \quad \text{expression (10)}$$

In expression (10), OL and $OL_+$ are position vectors of the point L and a point $L_+$ with the point O as the origin. Rot(φ, θ) is a rotation matrix expressed by expression (11) below, which rotates a three-dimensional position in the counter-clockwise direction around the x-axis by φ and in the counterclockwise direction around the y-axis by θ.

$$Rot(\phi, \theta) = \begin{pmatrix} \cos\theta & 0 & \sin\theta \\ 0 & 1 & 0 \\ -\sin\theta & 0 & \cos\theta \end{pmatrix} \cdot \begin{pmatrix} 1 & 0 & 0 \\ 0 & \cos\phi & -\sin\phi \\ 0 & \sin\phi & \cos\phi \end{pmatrix} \quad \text{expression (11)}$$

Similarly, points $A_+$ and $B_+$ at the left and right ends of a surface light source $L_+$ and an image capturing position $C_+$ with the plane normal line +5° inclined as a reference are calculated. By rotating the surface light source and the image capturing position by +5° in the direction opposite to the direction of the inclination of the plane normal line so that the plane normal line coincides with the z-axis, it is possible to calculate the surface light source and the image capturing position with the plane normal line as a reference. Further, the mirror image of the surface light source $L_+$ obtained by reflecting the surface light source $L_+$ symmetrically with respect to the x-axis around the center of the surface of the mirror body 1303 is taken to be $L_+'$, and the left and right ends of the mirror image $L_+'$ are taken to be points $A_+'$ and $B_+'$. From the calculated surface light source and image capturing position with the plane normal line as a reference, x-coordinates of intersections $P_-$ and $Q_+$ of straight lines connecting the points $A_+'$ and $B_+'$ and a center point $C_+$ of the camera lens, and the surface of the mirror body 1303 are calculated in accordance with expressions (12) and (13) below.

$$(0\ 0\ 1) \cdot (tOA_+' + (1-t)OC_+) = 0 \quad (0 < t < 1): \quad \text{expression (12)}$$

$$(0\ 0\ 1) \cdot (tOB_+' + (1-t)OC_+) = 0 \quad (0 < t < 1): \quad \text{expression (13)}$$

$OA_+'$, $OB_+'$, and $OC_+$ are position vectors of the points $A_+'$, $B_+'$, and $C_+$ in the case where the point O is taken to be the origin. Here, t is a parameter that takes a value between 0 and 1 and indicates position vectors of points on segments $A_+'C_+$ and $B_+'C_+$.

It is also possible to similarly calculate the range $R_+ < y < S_+$ in the y-direction, and the range $P_- < x < Q_-$ in the x-direction and the range $R_- < y < S_-$ in the y-direction in which the specularly reflected light of the surface light source enters the mirror body having a plane normal line −5° inclined. The measurement area setting unit 308 sets the rectangular common area within the calculated ranges in the x- and y-directions as a measurement area. The measurement area setting unit 308 stores measurement area data indicating the set measurement area in the storage area, such as the RAM 205, and the processing returns to the flowchart in FIG. 4 again.

As described above, in the image processing system 1 of the present embodiment, it is possible to efficiently acquire a gloss intensity distribution by calculating a measurement area of the gloss intensity distribution within the angle range set by a user from a subject having concavity/convexity. In the present embodiment, the measurement area is calculated from the range of the plane normal line of a subject set by a user, but it may also be possible to acquire the range of the plane normal line of a subject by a method other than the method that uses the setting input from a user. Further, the surface light source and the image capturing position with the plane normal line at the center of a subject as a reference are calculated and the surface light source and the image capturing position are regarded as being fixed within the measurement area, but it may also be possible to calculate the measurement area from the surface light source and the image capturing position with the plane normal line as a reference calculated for each point within the measurement area.

In the present embodiment, the area in which the specularly reflected light of the surface light source enters the mirror body and which is captured by the image capturing apparatus in the case where the mirror body is arranged at substantially the same position as that of a subject is set as a measurement area. However, the measurement area is not limited to the area in which the specularly reflected light of the surface light source enters the mirror body. For example, it may also be possible to set an area in which a difference between a combination of the pixel value and the gloss intensity at the center of a subject and a combination of the pixel value and the gloss intensity acquired under the conditions of the surface light source, the image capturing position, and the inclination of the plane normal line at each position on the subject is smaller than a predetermined threshold value as a measurement area.

In the present embodiment, the geometric attenuation term G is regarded as being the fixed value $G_0$ and it may also be possible to set a measurement area by the geometric attenuation term. For example, it may also be possible to set an area in which an error between the geometric attenuation term G due to the shade and shielding accompanying the minute concavity/concavity on a measurement sample and the fixed value $G_0$ in the case where the measurement sample is arranged at substantially the same position as that of the subject 100 is smaller than a predetermined threshold value as a measurement area. Further, the refractive index η on the subject surface is regarded as being equal within the surface and the Fresnel term F is regarded as being the fixed value $F_0$ and it may also be possible to set a measurement area by the Fresnel term. For example, it may also be possible to set an area in which an error between the Fresnel term F due to the Fresnel reflection on a measurement sample and the fixed value $F_0$ in the case where the measurement sample is arranged at substantially the same position as that of the subject 100 is smaller than a predetermined threshold value as a measurement area.

Third Embodiment

Figure 14:
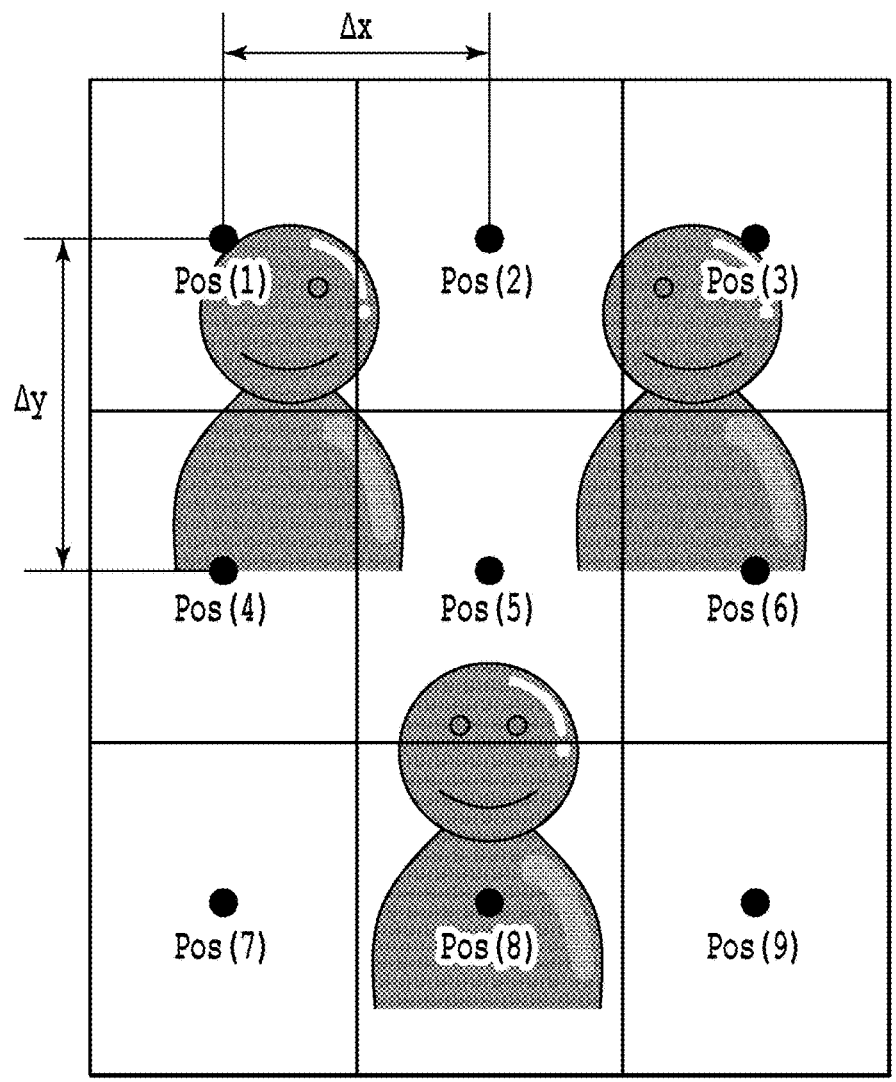
FIG. 14 is a schematic diagram showing an aspect in which an image capturing-target area of a subject changes in a third embodiment.

In the first and second embodiments, explanation is given to the method of acquiring a gloss intensity distribution of an image captured by the image capturing apparatus. In the present embodiment, explanation is given to a method of acquiring a gloss intensity distribution of a subject larger than the range that can be covered by the field angle of the image capturing apparatus by repeating movement of the subject by using a movable stage or the like. FIG. 14 is a schematic diagram showing an aspect in which the image capturing-target area of a subject placed on a movable stage changes as the movable stage moves in the present embodiment. As shown in FIG. 14, for example, by sequentially moving the movable stage to three points with a distance Δx in between in the x-direction and to three points with a distance Δy in between in the y-direction, that is, nine points in all, it is possible to acquire gloss intensity distribution image data at each subject position Pos (i). After acquiring each piece of gloss intensity distribution image data, by performing stitch processing of the gloss intensity distribution image data at each subject position Pos (i), it is possible to acquire a gloss intensity of a subject larger than the range that can be covered by the field angle of the image capturing apparatus 201.

Figure 15:
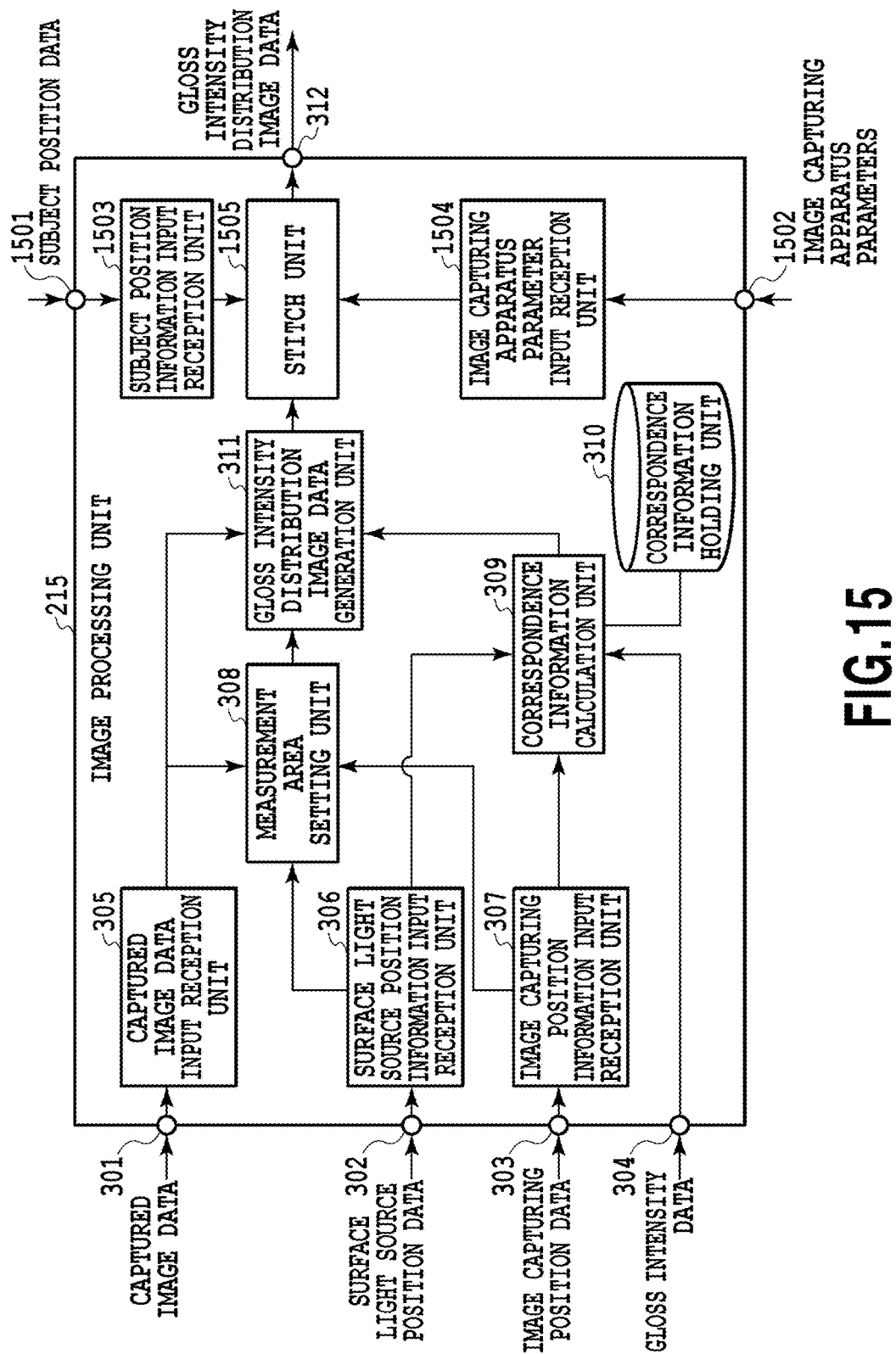
FIG. 15 is a software function configuration diagram of an image processing unit in the third embodiment.

FIG. 15 is a block diagram showing a software function configuration of the image processing unit 215 in the present embodiment. A processing procedure performed by image processing application software of the present embodiment based on instructions from the CPU 206 is explained with reference to FIG. 15. Explanation of the portions in common to those of the first embodiment is simplified or omitted and in the following, points unique to the present embodiment are explained mainly.

A subject position information input reception unit 1503 receives an input of subject position data and a signal indicating position information on a subject at the time of image capturing via an input terminal 1501. The subject position information whose input has been received is output to a stitch unit 1505. An image capturing apparatus parameter input reception unit 1504 receives an input of data and a signal indicating image capturing apparatus parameters at the time of image capturing via an input terminal 1502. The image capturing apparatus parameters whose input has been received are output to the stitch unit 1505. The stitch unit 1505 stitches each piece of gloss intensity distribution image data from the gloss intensity distribution image data at each subject position, the subject position information, and the image capturing apparatus parameters. The stitched gloss intensity distribution image data is output from the output terminal 312.

Figure 16:
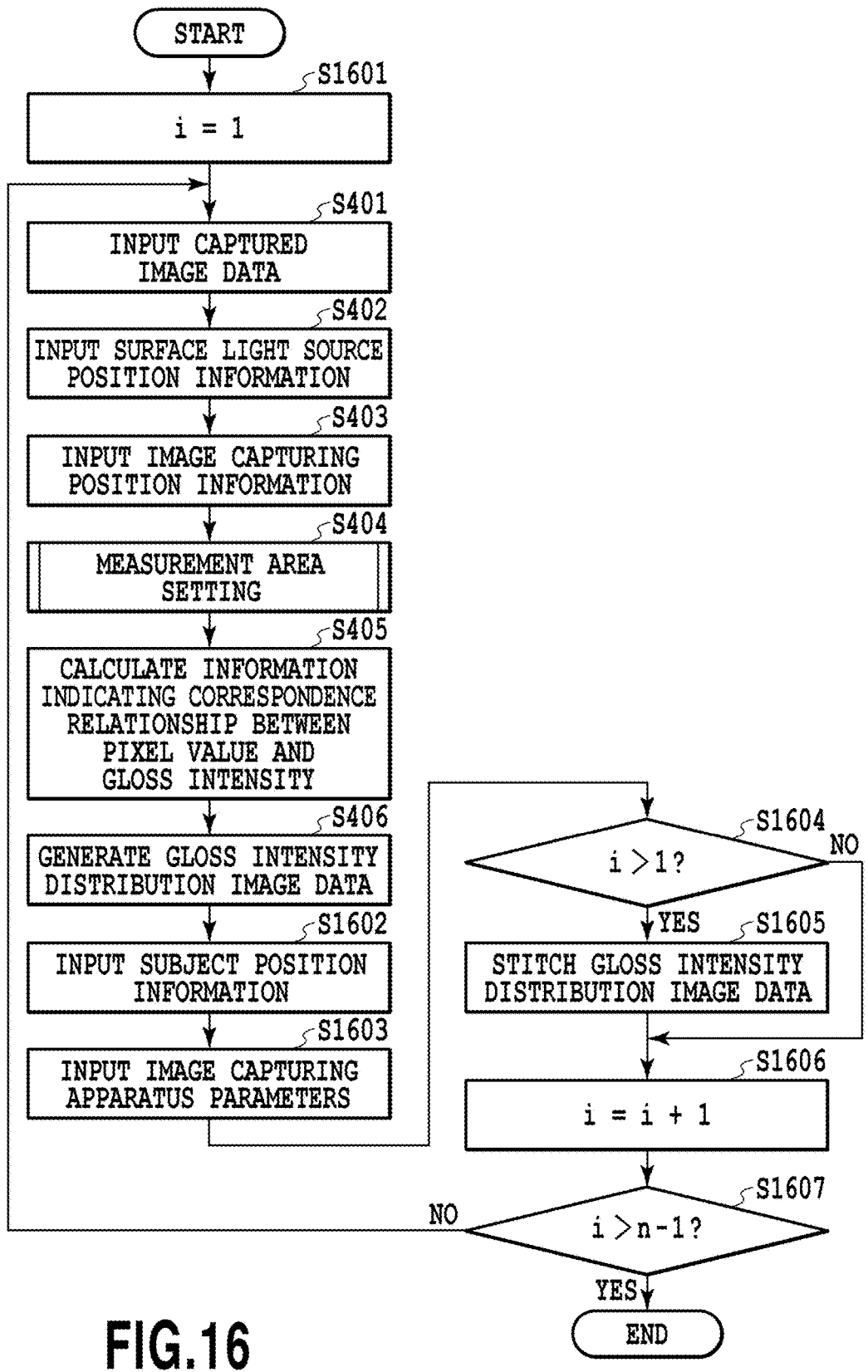
FIG. 16 is a flowchart showing an image processing procedure in the third embodiment.

Next, a processing procedure in the image processing unit 215 of the present embodiment is explained with reference to the flowchart in FIG. 16. The processing by the flowchart shown in FIG. 16 is performed by the CPU 206 loading the program codes stored in the ROM 204 and executing the program codes. Explanation of the portions in common to those of the first embodiment is simplified or omitted and in the following, points unique to the present embodiment are explained mainly.

At S1601, the subject position information input reception unit 1503 initializes a variable i indicating the order of image capturing of a subject. In the present embodiment, i is initialized to 1 (i=1).

S401 to S406 are the same as those of the first embodiment, and therefore, explanation is omitted. At S1602, the subject position information input reception unit 1503 receives an input of the position of the subject center at the time of the ith image capturing as the subject position data Pos (i). The subject position data Pos (i) whose input has been received is stored in the storage area, such as the RAM 205.

At S1603, the image capturing apparatus parameter input reception unit 1504 receives an input of the image capturing apparatus parameters at the time of the ith image capturing. Here, the image capturing apparatus parameters of the present embodiment are parameters indicating the image capturing characteristics of the image capturing apparatus 201, such as the focal length of the lens, the pixel position of the optical axis center, and the sensor pixel pitch. The image capturing apparatus parameters whose input has been received are stored in the storage area, such as the RAM 205.

At S1604, the stitch unit 1505 determines whether the variable i satisfies i>1. In the case where i>1 is satisfied, it is determined that the gloss intensity distribution image data at a plurality of subject positions can be stitched and the processing advances to S1605. In the case where i>1 is not satisfied, it is determined that the gloss intensity distribution image data at the first subject position has been acquired and the processing advances to S1606.

At S1605, the stitch unit 1505 performs geometric transformation for the gloss intensity distribution image data at Pos (i) by the publicly known projection transformation processing based on the subject position data and the image capturing apparatus parameters. Further, the stitch unit 1505 stitches the gloss intensity distribution image data at Pos (i)

for which the geometric transformation processing has been performed and the gloss intensity distribution image data at Pos (1) to Pos (i−1) having already been stitched by the publicly known α blending processing. The gloss intensity distribution image data for which the stitch processing has been performed is stored in the storage area, such as the RAM 205.

At S1606, the variable i is updated. In the present embodiment, i is incremented by 1 as i=i+1.

At S1607, the stitch unit 1505 determines whether the variable i satisfies i>n−1. In the case where it is determined that i>n−1 is satisfied, it is determined that the gloss intensity distribution image data at all the subject positions has been stitched and this flowchart is terminated. In the case where it is determined that i>n−1 is not satisfied, the processing returns to S401 again.

As explained above, in the present embodiment, it is possible to acquire a gloss intensity distribution of a subject larger than the range that can be covered by the field angle of the image capturing apparatus 201 at a high speed and with a high accuracy by repeating acquisition of a gloss intensity distribution and movement of the subject by using a movable stage or the like. In the present embodiment, by arranging a subject on a movable stage and moving the subject, a gloss intensity distribution of the subject larger than the range that can be covered by the field angle of the image capturing apparatus 201 is acquired, but it may also be possible to fix a subject and move the surface light source and the camera. Further, by using the subject position and the image capturing apparatus parameters, geometric transformation is performed for the gloss intensity distribution image data at each subject position by projection transformation, but it may also be possible to perform geometric transformation by detecting a corresponding point of each piece of gloss intensity distribution image data by using the publicly known template matching and SIFT method.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

It is possible for the image processing apparatus of the present invention to efficiently acquire a gloss intensity distribution of a subject from a subject having concavity/convexity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-105514 filed May 26, 2016, which is hereby incorporated by reference wherein in its entirety.

What is claimed is:

1. An image processing apparatus that generates gloss intensity distribution image data indicating a gloss intensity distribution based on captured image data obtained by capturing an image of a subject having concavity/convexity irradiated by a surface light source, the image processing apparatus comprising:

a setting unit configured to set an area, in which specularly reflected light in a virtual planar mirror for entered light from the surface light source is received by an image capturing apparatus and which is a same size as or smaller than that of an area captured by the image capturing apparatus in a case where the virtual planar mirror is arranged at the same position as that of the subject, as a measurement area of the gloss intensity distribution; and a generation unit configured to generate the gloss intensity distribution image data in the measurement area based on pixel values of the captured image data.

2. The image processing apparatus according to claim 1, wherein the setting unit sets an area, in which specularly reflected light in a virtual mirror body for entered light from the surface light source is received by an image capturing apparatus and which is the same size as or smaller than that of an area captured by the image capturing apparatus in a case where the virtual mirror body having a plane normal line is arranged at the same position as that of the subject, as the measurement area based on surface light source position information indicating the position of the surface light source, image capturing position information indicating the position of the image capturing apparatus that captures an image of the subject, and plane normal line range information indicating an angle range of the plane normal line of the subject.

3. The image processing apparatus according to claim 2, wherein the plane normal line range information indicates an angle range of a plane normal line of the subject, whose input has been received from a user.

4. The image processing apparatus according to claim 1, further comprising:

a stitch unit configured to perform stitch processing for a plurality of pieces of gloss intensity distribution image data generated from a plurality of pieces of captured image data obtained by capturing images at a plurality of positions on the subject.

5. The image processing apparatus according to claim 1, wherein the generation unit refers to information indicating correspondence relationship between pixel value and gloss intensity in which the pixel value and the gloss intensity are associated with each other and converts the pixel value at each pixel position in the image data into the gloss intensity.

6. The image processing apparatus according to claim 1, further comprising:
an input reception unit configured to receive an input of a gloss intensity that serves as a reference; and
a correspondence information calculation unit configured to calculate the information indicating correspondence relationship between pixel value and gloss intensity by calculating a value obtained by integrating Bidirectional Reflectance Distribution Function in an angle area in which light from the surface light source enters the subject as the pixel value and by associating the gloss intensity that serves as a reference with the calculated pixel value based on surface light source position information indicating the position of the surface light source, image capturing position information indicating the position of the image capturing apparatus that captures an image of the subject, and the gloss intensity that serves as a reference.

7. The image processing apparatus according to claim 6, wherein
the information indicating correspondence relationship between pixel value and gloss intensity is calculated for each image capturing condition specified by the surface light source position information and the image capturing position.

8. An image processing apparatus that generates gloss intensity distribution image data indicating a gloss intensity distribution based on captured image data obtained by capturing an image of a subject having concavity/convexity irradiated by a surface light source, the image processing apparatus comprising:
a setting unit configured to set an area, in which an error of a geometric attenuation term due to shade and shielding accompanying concavity/convexity on a measurement sample in a case where the measurement sample is arranged at the same position as that of the subject is smaller than a predetermined threshold value, as a measurement area of the gloss intensity distribution based on surface light source position information indicating the position of the surface light source and image capturing position information indicating the position of the image capturing apparatus that captures an image of the subject; and
a generation unit configured to generate the gloss intensity distribution image data in the measurement area based on the surface light source position information, the image capturing position information, and pixel values of the captured image data.

9. An image processing apparatus that generates gloss intensity distribution image data indicating a gloss intensity distribution based on captured image data obtained by capturing an image of a subject having concavity/convexity irradiated by a surface light source, the image processing apparatus comprising:
a setting unit configured to set an area, in which an error of a Fresnel term due to Fresnel reflection on a measurement sample in a case where the measurement sample is arranged at the same position as that of the subject is smaller than a predetermined threshold value, as a measurement area of the gloss intensity distribution based on surface light source position information indicating the position of the surface light source and image capturing position information indicating the position of the image capturing apparatus that captures an image of the subject; and
a generation unit configured to generate the gloss intensity distribution image data in the measurement area based on the surface light source position information, the image capturing position information, and pixel values of the captured image data.

10. An image processing method of generating gloss intensity distribution image data indicating a gloss intensity distribution based on captured image data obtained by capturing an image of a subject having concavity/convexity irradiated by a surface light source, the image processing method comprising:
setting an area, in which specularly reflected light in a virtual planar mirror for entered light from the surface light source is received by an image capturing apparatus and which is a same size as or smaller than that of the area captured by an image capturing apparatus in a case where the virtual planar mirror is arranged at the same position as that of the subject, as a measurement area of the gloss intensity distribution; and
generating the gloss intensity distribution image data in the measurement area based on pixel values of the captured image data.

11. A non-transitory computer readable storage medium storing a program for causing a computer to function as an image processing apparatus that generates gloss intensity distribution image data indicating a gloss intensity distribution based on captured image data obtained by capturing an image of a subject having concavity/convexity irradiated by a surface light source, wherein,
the image processing apparatus comprises:
a setting unit configured to set an area, in which specularly reflected light in a virtual planar mirror for entered light from the surface light source is received by an image capturing apparatus and which is a same size as or smaller than that of an area captured by the image capturing apparatus in a case where the virtual planar mirror is arranged at the same position as that of the subject, as a measurement area of the gloss intensity distribution; and
a generation unit configured to generate the gloss intensity distribution image data in the measurement area based on the pixel values of the captured image data.

12. The image processing apparatus according to claim 1, further comprising:
a input unit configured to input surface light source position information indicating a position of the surface light source and image capturing position information indicating a position of an image capturing apparatus that captures an image of the subject;
wherein the setting unit configured to set the measurement area based on the surface light source position information and the image capturing position information;
wherein the generation unit configured to generate the gloss intensity distribution image data in the measurement area based on the surface light source position information, the image capturing position information, and pixel values of the captured image data.

13. The image processing apparatus according to claim 12, wherein the surface light source position information further indicates a direction of the surface light source;
wherein the setting unit sets the measurement area corresponding to the direction of the surface light source.

14. The image processing apparatus according to claim 1, wherein the generation unit generates the gloss intensity distribution image data in the measurement area based only on a pixel value in the pixel values of the captured image data corresponding to the measurement area set by the setting unit.

15. The image processing apparatus according to claim 1, wherein the measurement area is smaller than that of an area captured by the image capturing apparatus.

16. The image processing apparatus according to claim 1, wherein the measurement area is an area surrounded by a position where light from a light source at an end of the surface light source is reflected from the virtual planar mirror, and is received by the image capturing apparatus.

17. The image processing apparatus according to claim 1, wherein the measurement area is an area that reflected light in the subject for entered light from the surface light source is received by the image capturing apparatus under specular reflection.

* * * * *